United States Patent [19]

Hutchins

[11] Patent Number: 5,419,754

[45] Date of Patent: May 30, 1995

[54] KNEE BRACE

[75] Inventor: Stephen Hutchins, Chester, United Kingdom

[73] Assignee: Robert Johnson, Hoylake, United Kingdom; a part interest

[21] Appl. No.: 191,914

[22] Filed: Feb. 4, 1994

[30] Foreign Application Priority Data

Feb. 5, 1993 [GB] United Kingdom ............... 9302227
Feb. 15, 1993 [GB] United Kingdom ............... 9303018
Mar. 12, 1993 [GB] United Kingdom ............... 9305104

[51] Int. Cl.[6] .................................................... A61F 5/00
[52] U.S. Cl. ............................................. 602/16; 602/26
[58] Field of Search ......................... 602/5, 16, 23, 26; 2/16, 24, 62

[56] References Cited

U.S. PATENT DOCUMENTS

| | | |
|---|---|---|
| 2,883,982 | 4/1959 | Rainey . |
| 4,088,130 | 5/1978 | Applegate ........................ 602/26 X |
| 4,372,298 | 2/1983 | Lerman ............................... 602/26 |
| 4,493,316 | 1/1985 | Reed et al. ...................... 602/26 X |
| 4,520,802 | 6/1985 | Mercer et al. .................. 602/26 X |
| 4,524,764 | 6/1985 | Miller et al. ................... 602/26 X |
| 4,633,867 | 1/1987 | Kausek et al. .................... 602/26 |
| 4,643,176 | 2/1987 | Mason et al. . |
| 4,697,583 | 10/1987 | Mason et al. ..................... 602/26 |
| 4,844,057 | 7/1989 | Hoy .................................... 602/16 |
| 5,038,763 | 8/1991 | Wiggins . |
| 5,060,640 | 10/1991 | Rasmusson ....................... 602/26 X |
| 5,062,858 | 11/1991 | Broeck et al. .................. 602/16 X |

FOREIGN PATENT DOCUMENTS 0070411 1/1983 European Pat. Off. .
0401170 5/1990 European Pat. Off. .
671876 10/1989 Switzerland .
2161388 1/1986 United Kingdom .

Primary Examiner—Linda C. M. Dvorak
Attorney, Agent, or Firm—Dennison, Meserole, Pollack & Scheiner

[57] ABSTRACT

A knee brace comprising upper and lower leg-engaging/embracing parts (thigh and calf pieces) connectable around upper and lower parts of the leg above and below the knee joint with the upper and lower leg embracing parts having upper and lower brace members respectively interconnected by at least one joint, wherein the at least one joint means each comprises at least one link member pivotally connected at pivot points to rotate about a pivotal axis on each of the brace members with the at least one link member being provided for holding brace members together, and wherein the end region of a first said brace member has a slot defined between two end arm portions and within the slot space or forming a defining portion thereof, a first gear is provided and such is engaged by a second gear on the end of the second brace member which second gear is displaceable in the slot to engage the first gear and wherein the first and second gears each lie on arcs each concentric with the pivot point of the brace member on which the respective gear is provided, and with the arc of the normally upper brace member being on a smaller radius than the other so that the upper brace member rotates at a faster angular velocity than the lower brace member to proximate the movement of a knee joint.

19 Claims, 4 Drawing Sheets

KNEE BRACE

BACKGROUND OF THE INVENTION

The present invention relates to an improved knee brace having good stability.

Whilst the knee brace is primarily intended for orthopaedic use, the brace may be used as a prophylactic device for use in sport, for example, in skiing and wherein two joint means are provided one either side of the knee joint.

SUMMARY OF THE INVENTION

It is an object of the present invention to provide an improved knee brace wherein the lateral stability is enhanced and preferably one wherein the movement more closely proximates that of a knee joint.

According to the present invention there is provided an improved knee brace comprising upper and lower leg-engaging/embracing parts (thigh and calf pieces) connectable around upper and lower parts of the leg above and below the knee joint with the upper and lower leg embracing parts having upper and lower brace members respectively interconnected by at least one joint means, wherein the at least one said joint means each comprises at least one link member pivotally connected to of said brace members for holding said brace members together, wherein first and second gear means are provided on the upper and lower brace members and lie on arcs with the arc of the upper brace member having a smaller radius than the arc of the lower member and the gear means are such that the upper brace member rotates at a faster angular velocity than the lower so as to closely resemble the movement of a knee joint.

Also according to the present invention there is provided an improved knee brace comprising upper and lower leg-engaging/embracing parts (thigh and calf pieces) connectable around upper and lower parts of the leg above and below the knee joint with the upper and lower leg embracing parts having upper and lower brace members respectively interconnected by at least one joint means, wherein the at least one said joint means each comprises at least one link member pivotally connected to each of said brace members for holding such together, wherein the end region of the normally upper brace member has a slot or passage therein defined between two arm portions of said member and in which slot a first gear means is provided comprising a series of cross members, preferably in the form of short cylinders or pins, arranged on an arc on a first radius which does not extend beyond the end of said upper member and wherein the end region of the lower brace member is provided with a second gear means formed as a series of recesses cooperably receiving said cross members and arranged as an arc on a second radius which is longer than the radius of said first arc and the gear means such that the upper brace member moves at a greater angular displacement relative to the lower brace member so as to resemble the movement of the parts of a normal human knee joint.

Also according to the present invention there is provided an improved knee brace comprising upper and lower leg-engaging/embracing parts (thigh and calf pieces) connectable around upper and lower parts of the leg above and below the knee joint with the upper and lower leg embracing parts having upper and lower brace members respectively interconnected by at least one joint means, characterised by the feature that said joint means each comprises at least one link member pivotally connected at pivot points to rotate about a pivotal axis on each of said brace members with said at least one link member being provided for holding said brace members together, and wherein the end region of a first said brace member has a slot defined between two end arm portions and within the slot space or forming a defining portion thereof, a first gear means is provided and such is engaged by second gear means on the end of the second brace member which second gear means is displaceable in said slot to engage said first gear means; and wherein said first and second gear means lie on arcs each concentric with the pivot point of the brace member on which it is provided and with the arc of the upper brace member being on a smaller radius than the other so that together with the characteristics of the gear means the upper brace member rotates at a faster angular velocity than the lower to proximate the movement of a knee joint.

Preferably the gear means of the second or lower brace member is an arcuate or otherwised curved or shaped portion and provided having a plurality of spaced apart curved or otherwise shaped recesses each for temporarily receiving a crank, pin, cross piece integrally formed gear means or other drive means arcuately or otherwise on the lower, first brace member.

The link and gear means forms a planetary hinge or gear preferably with slot and pin action. It has been found particularly advantageous for the pins, other cross members or other drive means of the first, upper brace member to be spaced closer to the pivotal axis of the link member on said first upper, member so that when the brace members are moved concurrently the upper, first brace member rotates at a faster angular velocity than the lower, second brace member - thereby more closely proximating the movement of an actual knee joint. Thus the gear means on the upper brace member is disposed on an arc of smaller radius than the gear means of the lower brace member and the gear means such that the upper joint part is displaced more than the lower. The selection of the pitch and/or gear ratio to achieve the desired movement is of importance. It is considered that any gear means therefor which achieves such effect would also fall within the scope of the present invention. It is even envisaged that the gear means may be a Geneva mechanism which will produce intermittent motion.

Preferably the upper, first brace member which is to have the pins or other drive means of the gear means is formed so as to have the bifurcated end wherein in the slot thus defined said pins extend thereacross and are secured so as to act to hold the arms together to prevent or minimize lateral flexing. The slotted/recessed portion of the gear means being provided on the end of the lower, second brace member and being displaceable in the slot provided by the bifurcated ends of the first member and preferably in close relationship to provide a stable interrelationship. The arrangement provides good lateral stability on all positions of the joint so as to facilitate the joint to withstand lateral impacts. Preferably the upper brace member with the bifurcated end is integrally formed, for example, by moulding or otherwise formed from plastics or like material or by machining from a solid part such as a metal part.

It is envisaged that whilst the upper brace part is referred to as being bifurcated, such feature may instead be provided on the lower, second brace member but with the gear pitches and/or ratios being modified to achieve the desired angular displacement.

The adjacent ends of the actual brace members (other than such forming the gear means portion) will not be in a rolling abutment although may be in abutment in one end position as a stop to prevent hyperextension.

It is considered desirable and preferable for at least two pins or other drive means of the gear means to always be engaged in two recesses or slots or be closely moving into such relationship.

For each joint means, two link members will preferably be provided one on opposite sides of the ends of the brace or joint members and sandwiching the gear means therebetween.

As mentioned above, it is a desirable feature that the gear mechanism is constructed such that when the brace parts are moved concurrently the two arms move at different velocities or angular displacements.

It is to be appreciated that whilst reference is made herein to the joint means interconnecting brace members, it is also envisaged, that such brace members may instead be joint parts which themselves are connected to or connectable to said brace members.

Whilst the knee brace of the present invention may have a single joint means for location on one side of the knee joint, it is preferable that the knee brace will incorporate two such joints locatable one either side of the knee joint for increased stability and support.

Preferably range of motion facility will be provided to limit the movement to prevent hyperextension and preferably such will be adjustable. Suitable stop surfaces may be provided in the side plates and/or on the adjacent surfaces of the joint members.

The present invention has been described in relation to a knee brace but is also intended to be of such scope as to cover the joint per se.

The invention will be described further, by way of example, with reference to the accompanying drawings;

DESCRIPTION OF PREFERRED EMBODIMENT

Figure 1:
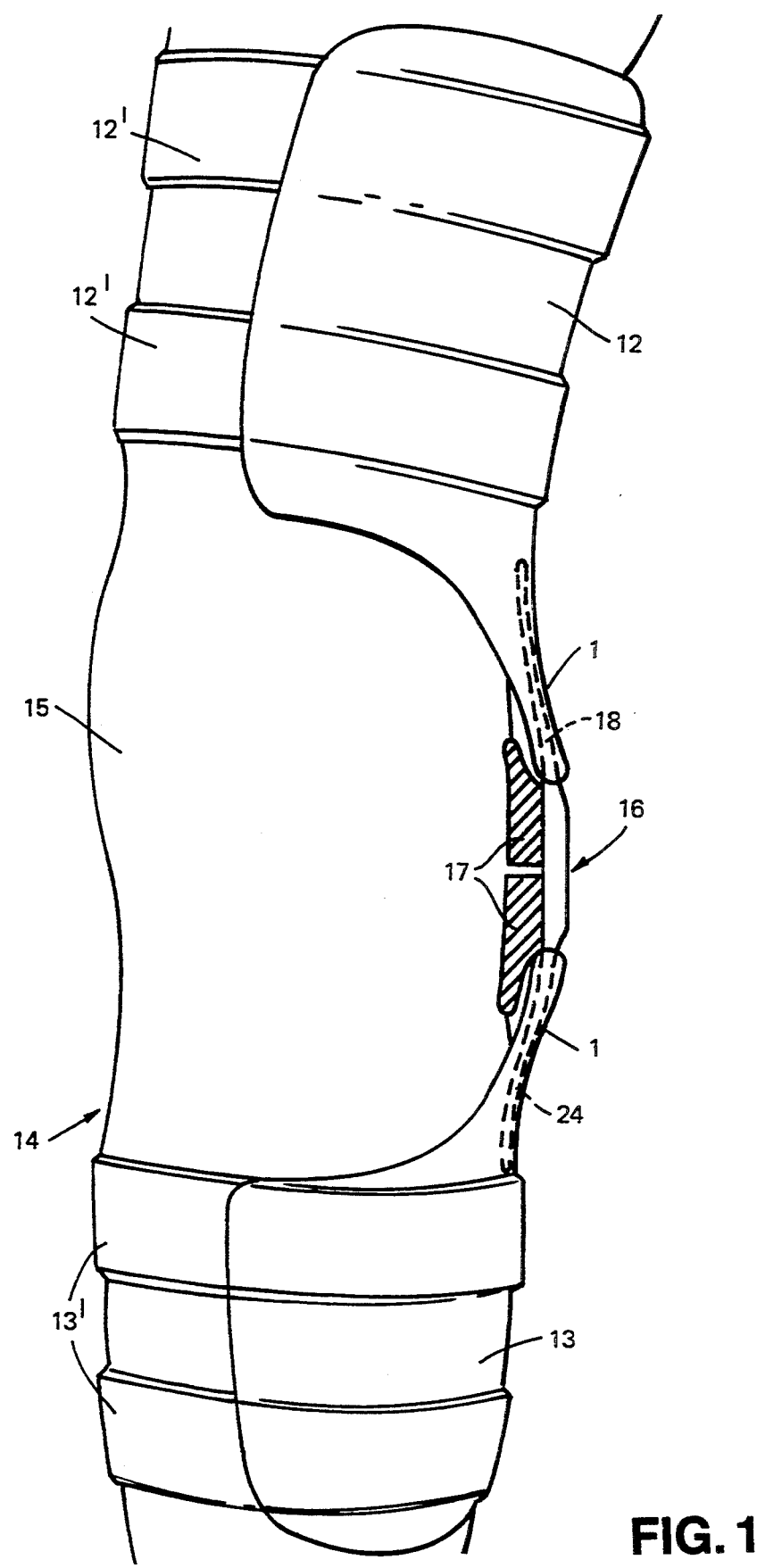
FIG. 1 is a general schematic front elevation of a knee brace forming one embodiment of the invention and wherein only a single joint is illustrated connecting the brace members which are slightly curved in this view.
Figure 2:
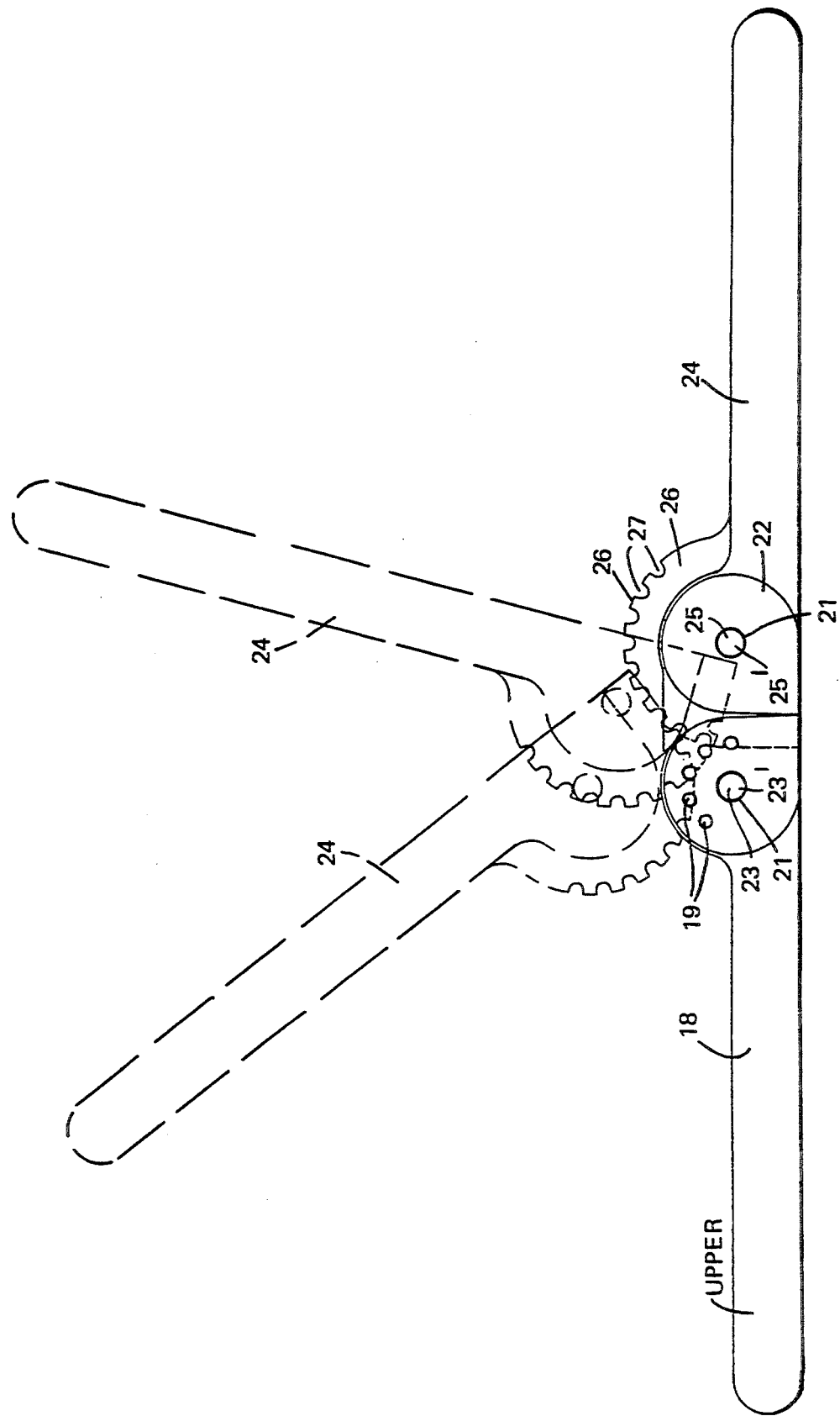
FIG. 2 is a schematic elevation of two straight brace members held together by a link member and illustrating a gear means and showing the different positions of movement caused thereby.
Figure 3:
FIG. 3 is a plan view of an upper brace member having a bifurcated end portion.
Figure 5:
FIG. 5 is an end elevation in the direction of arrow B.
Figure 4:
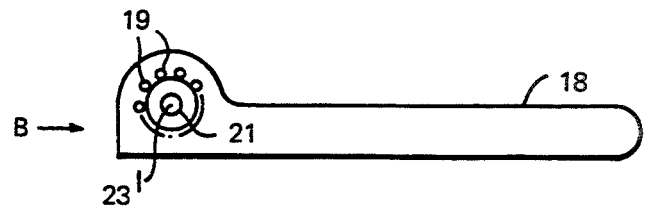
FIG. 4 is a vertical section along the line A-A of FIG. 3.
Figure 7:
FIG. 7 is an end elevation of the lower brace member of FIG. 6 in the direction of arrow C and when located between the arms of the bifurcated brace member.
Figure 6:
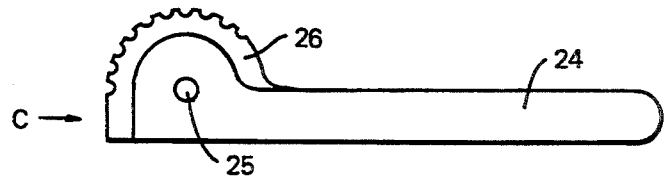
FIG. 6 is a side elevation of the lower brace member illustrating the slotted/recessed portion of the gear means.
Figure 8:
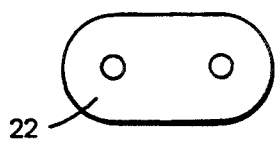
FIG. 8 is an elevation illustrating the link member.
Figure 9:
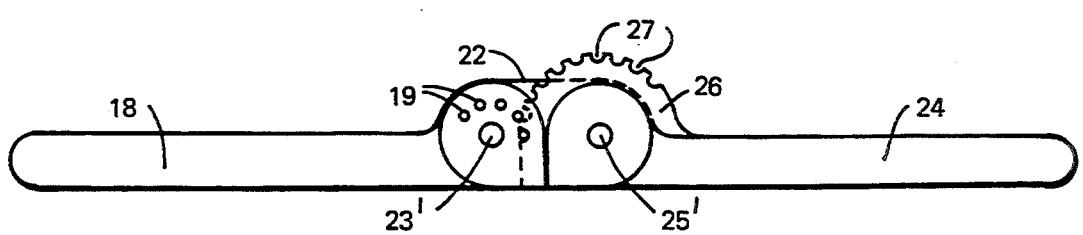
FIG. 9 is an elevation showing the two brace members and link member interconnected and forming a planetary gear and driven via the gear means.

A knee brace 11 is illustrated in FIG. 1 comprising a thigh cup 12 with associated securing straps 12' and a calf piece 13 with associated securing straps 13'. A user's left leg 14 is partially illustrated in broken line with the knee cap region being at 15. A joint 16 according to the invention is generally indicated with brace members 1 thereof being fixedly secured to cup 12 and piece 13. Two cushion pads 17 are provided on the inner sidle of joint 16 between such and knee 15.

The brace members and gear means illustrated in FIGS. 2-9 are of a preferred embodiment and comprise an upper part brace part or member 18 formed as a single piece, e.g. by machining or moulding, and having a plurality of pins or like drive means 19 with the gear forming parts being arcuately arranged wholly within the slot 20 defined by the bifurcation and acting to hold the arms 18' of the bifurcation together. Preferably the pins 19 will comprise screwed in metal parts which provide additional stability for the end of the brace member 18 which is preferably formed of a strong material such as carbon fibre or nylon.

An aperture 21 is provided concentrically with the arc of the pin arrangement and two link members 22 (only one shown) are pivotally connected therewith, via pivot pins 23 in known manner on opposite sides of brace member 18 and also pivotally connected via pivot 25 extending through a lower brace member 24 and on opposite sides thereof.

The lower brace member 24 is formed having an arcuate portion 26 fixed/stationary relative thereto by being integrally formed and having a plurality of curved recesses or slots 27 on the outer edge thereof which are shaped and dimensioned and spaced so as to engage with the pins 19 of the upper brace member 18 and thereby form the gear means. Preferably the gear means is such that two pins will engage in the recesses at any one time or be approximating such engagement such that continuous movement is achieved. For example, pins may be provided every 15° (although with a Geneva mechanism the spacing may be at every 28°).

The arcuate portion 26 and adjacent portions fit closely between the arms 18' with minimal spacing such that additional stability for the arrangement is advantageously obtained.

Also preferably, the spacing between the pins 19 and the axis of rotation 23' of the upper base member 18 on which they are located is less than the spacing from axis of rotation 25' of the adjacent brace member so as to thereby achieve a movement wherein the upper brace member 18 rotates at faster angular velocity than the lower brace member. Thus when the brace parts are moved concurrently, the two brace members 18,24 move at different velocities and thereby more closely approximate the movement of a knee joint.

Figure 10:
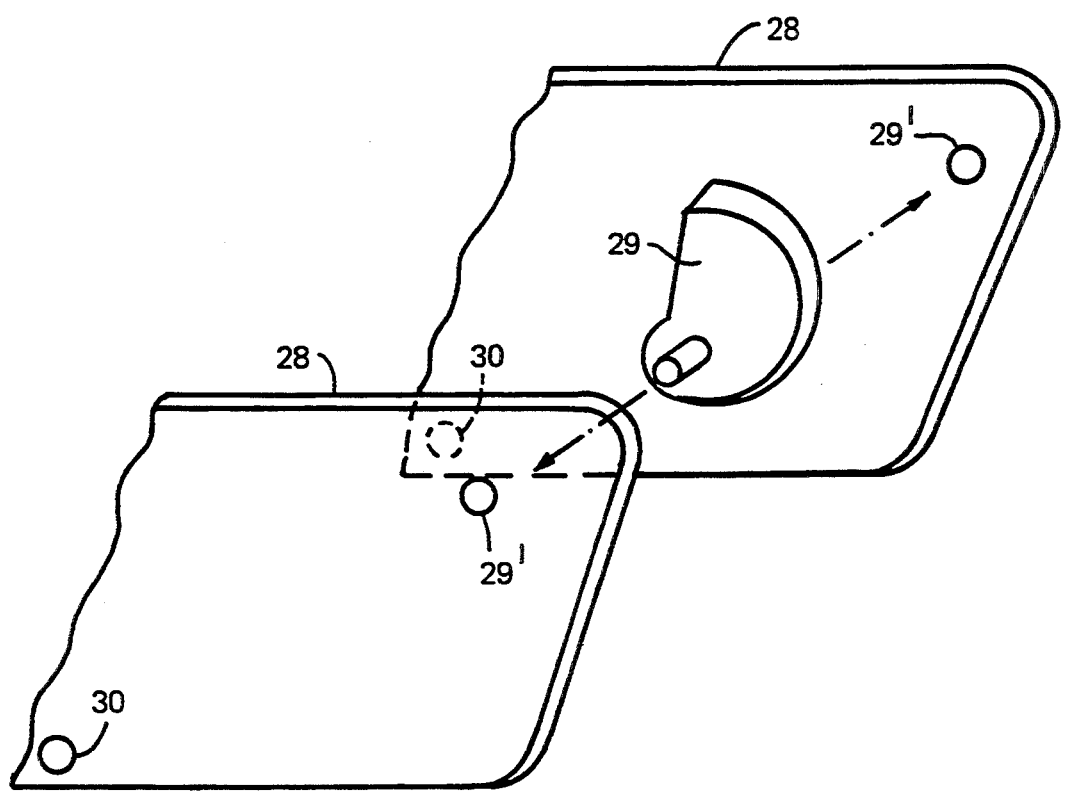
FIG. 10 is a schematic view showing a range of motion limiting means in the form of oppositely disposed adjustable cams on the link members.

In FIG. 10 the ends of two link members 28 are illustrated in enlarged scale and spaced apart. A spiral cam 29 is rotatably and adjustably mounted at 29' and sandwiched between the two members 28 to abut the edge of a brace member. A second identical or similar spiral cam (not shown) is similarly rotatably adjustably mounted at 30 in the diagonally opposite corner so that the spiral cams will limit motion in each direction of movement of the joint means to restrict flexion but are adjustable in position of fixing to enable the range of movement to be adjacent. The spiral cams in the diagonal corners between the two side plates or link members 28 when turned, will abut against edges of the brace members sooner as the radius increases—so providing limiting of motion for the joint means i.e. restricting flexion. Also, their position will strengthen the joint by holding the link members together in diagonal corners.

According to a different aspect of the present invention concerning primarily lateral stability there is provided an improved knee brace comprising upper and lower leg-engaging/embracing parts (thigh and calf pieces) connectable around upper and lower parts of the leg above and below the knee joint with the upper and lower leg embracing parts having upper and lower brace members respectively interconnected by at least one joint means, wherein the at least one said joint means comprises at least one link member pivotally connected at pivot points to rotate about a pivotal axis on each of said brace members with said at least one link member being provided for holding said brace members together and maintaining gear means thereof interengaged; and wherein the end region of a first said brace member has a slot defined between two end arm portions and within said slot space a portion of the end of the second brace member is displaceable in close proximity to said arms so as to act to restrict lateral displacement of the joint means. Preferably the gear means is provided within the slot and on the end of the second brace member.

Preferably the gear means of the second or lower brace member of this different aspect is an arcuate or otherwised curved or shaped portion and provided having a plurality of spaced apart curved or otherwise shaped recesses each for temporarily receiving a crank, pin, cross piece, integrally formed gear means or other drive means arcuately or otherwise on the lower, first brace member.

The link and gear means of this aspect also form a planetary hinge or gear preferably with slot and pin action and preferably as hereinbefore described.

I claim:

1. A knee brace comprising upper and lower leg-embracing parts connectable around upper and lower parts of the leg above and below the knee joint with the upper and lower leg embracing parts having upper and lower brace members with ends respectively interconnected by at least one joint means, wherein said at least one joint means comprises at least one link member pivotally connected at pivot points to said upper and lower brace members to permit relative rotation about a pivotal axis with respect to each of said brace members with said at least one link member being provided for holding said brace members together, and wherein the end region of a first said brace member has a slot defined between two end arm portions and within the slot space or forming a defining portion thereof, a first gear means is provided and such is engaged by second gear means on the end of the second brace member which second gear means is displaceable in said slot to engage said first gear means; and wherein said first and second gear means each lie on arcs each concentric with the pivot point of the brace member on which the respective gear means is provided, and with the arc of the normally upper brace member being on a smaller radius than the other so that the upper brace member rotates at a faster angular velocity than the lower brace member to proximate the movement of a knee joint.

2. A brace as claimed in claim 1, in which the gear means of the second brace member has a plurality of spaced apart recesses forming said second gear means each for temporarily receiving projecting portions forming said first gear means of said first brace member. forming said first gear means of said first brace member.

3. A brace as claimed in claim 1, in which the link and gear means form a planetary hinge with slot and pin action.

4. A brace as claimed in claim 1, in which the first brace member has cross pieces which extend between the arm portions and are secured thereto so as to act to hold the arms together to prevent or minimise lateral flexing.

5. A brace as claimed in claim 1, in which the first brace member with the slot in its end region is integrally formed.

6. A brace as claimed in claim 1, in which the adjacent ends of the brace members other than such forming the gear means portions are not in rolling abutment.

7. A brace as claimed in claim 1, in which the adjacent ends of the brace members are only in abutment in one end position as a stop to prevent hyperextension.

8. A brace member as claimed in claim 1, in which at least two drive means of the gear means are always engaged in two recesses or are closely moving into such relationship.

9. A brace as claimed in claim 1, in which for each joint means, two link members are provided on opposite sides of the ends of the brace members and sandwiching at least parts of the end arm portions of the first brace member therebetween.

10. A brace as claimed in claim 1, in which said brace members are instead joint parts which themselves are connectable to brace members.

11. A brace as claimed in claim 1, in which two joint means are provided locatable on either side of the knee joint for increased stability and support.

12. A brace as claimed in claim 1, in which range of motion means are provided to limit the movement to prevent hyperextension and comprise stop surfaces.

13. A brace as claimed in claim 12, in which said surfaces are adjustable in position to adjust the ranged motion means.

14. A knee brace comprising upper and lower leg-embracing parts connectable around upper and lower parts of the leg above and below the knee joint with the upper and lower leg embracing parts having upper and lower brace members respectively interconnected by at least one joint means, wherein said at least one joint means comprises at least one link member pivotally interconnecting said brace members for holding such together, wherein an end region of the normally upper brace member has a passage therein defined between two arm portions of said member and in which passage a first gear means is provided comprising a series of cross members, arranged on an arc on a first radius which does not extend beyond the end region of said upper member and wherein an end region of the lower brace member is provided with a second gear means formed as a series of recesses cooperably receiving said cross members and arranged as an arc on a second radius which is longer than the radius of said first arc and the gear means such that the upper brace member moves at a greater angular displacement relative to the lower brace member so as to resemble the movement of the parts of a normal human knee joint.

15. A knee brace comprising upper and lower leg-embracing parts connectable around upper and lower parts of the leg above and below the knee joint with the upper and lower leg embracing parts having upper and lower brace members respectively interconnected by at least one joint means, wherein said at least one joint means comprises at least one link member pivotally connected at pivot points to permit relative rotation about a pivotal axis on each of said brace members with said at least one link member being provided for holding said brace members together and maintaining gear means thereof interengaged; and wherein an end region of a first said brace member has a slot defined between two end arm portions and within said slot space a portion of an end of the second brace member is displaceable in close proximity to said arms so as to act to restrict lateral displacement of the joint means.

16. A brace as claimed in claim 15, in which gear means are provided within the slot of said first brace member and on the end of the second brace member.

17. A device as claimed in claim 15, in which the gear means of the second brace member is a shaped portion having a plurality of spaced apart shaped recesses each for temporarily receiving drive means found on the first brace member.

18. A device as claimed in claim 15 in which the link and gear means forms a planetary gear with slot and pin action with the pins of the first, upper brace member spaced closer to the pivotal axis of the link member on said first member so that when the brace members are moved concurrently the upper, first brace member rotates at a faster angular velocity than the lower, second brace member.

19. A knee brace comprising upper and lower leg-embracing parts connectable around upper and lower parts of the leg above and below the knee joint with the upper and lower leg embracing parts having upper and lower brace members respectively interconnected by at least one joint means, wherein said joint means comprises at least one link member pivotally interconnecting said brace members for holding said brace members together, wherein first and second gear means are provided on the upper and lower brace members and lie on arcs with the arc of the upper brace member having a smaller radius than the arc of the lower member and the gear means are such that the upper brace member rotates at a faster angular velocity than the lower so as to closely resemble the movement of a knee joint.

* * * * *